(12) United States Patent
Gunasekar et al.

(10) Patent No.: US 11,166,673 B2
(45) Date of Patent: Nov. 9, 2021

(54) ELECTROENCEPHALOGRAPHY HEADSET AND SYSTEM FOR COLLECTING BIOSIGNAL DATA

(71) Applicant: Zeto, Inc., Santa Clara, CA (US)

(72) Inventors: Aswin Gunasekar, San Jose, CA (US); Gabor Braun, Salgótarján (HU); Ferenc Benedek, Szeged (HU); János Kokavecz, Kiskoros (HU); Joshua Morenstein, San Francisco, CA (US); Christopher HibmaCronan, Oakland, CA (US); Drew Putterman, Oakland, CA (US); Chris Fruhauf, Sunnyvale, CA (US); Brian Tachibana, Sunnyvale, CA (US); Max Guangqun Chen, Sunnyvale, CA (US); Lauren Margolin, Sunnyvale, CA (US)

(73) Assignee: Zeto, Inc., Santa Clara, CA (US)

( * ) Notice: Subject to any disclaimer, the term of this patent is extended or adjusted under 35 U.S.C. 154(b) by 0 days.

(21) Appl. No.: 16/880,953

(22) Filed: May 21, 2020

(65) Prior Publication Data

US 2020/0281527 A1    Sep. 10, 2020

Related U.S. Application Data

(63) Continuation of application No. 15/831,143, filed on Dec. 4, 2017.

(Continued)

(51) Int. Cl.
*A61B 5/00* (2006.01)
*A61B 5/291* (2021.01)

(52) U.S. Cl.
CPC ............ *A61B 5/6803* (2013.01); *A61B 5/291* (2021.01); *A61B 2562/0209* (2013.01); *A61B 2562/043* (2013.01); *A61B 2562/046* (2013.01)

(58) Field of Classification Search
CPC .................. A61B 5/683; A61B 5/0478; A61B 2562/0209; A61B 2562/043; A61B 2562/046

(Continued)

(56) References Cited

U.S. PATENT DOCUMENTS 4,112,941 A  *   9/1978   Larimore ............. A61B 5/0416
                                                            600/394
4,640,290 A  *   2/1987   Sherwin ............... A61B 5/0478
                                                            600/382

(Continued)

*Primary Examiner* — Linda C Dvorak
*Assistant Examiner* — Annabeth E Rodriguez
(74) *Attorney, Agent, or Firm* — Run8 Patent Group, LLC; Peter Miller; Ryan B. Kennedy

(57) ABSTRACT

One variation of a system for collecting biosignal data includes: a left junction; a right junction; a first band spanning the left and right junctions; a first band adjuster configured to adjust a length of the first band between the left and right junctions; a second band spanning the left and right junctions and radially offset from the first band about a lateral axis spanning the left and right junctions; a second band adjuster configured to adjust a length of the second band between the left and right junctions; a first electrode fixedly mounted to the first band and centered between the left and right junctions; a second electrode mounted to the first band offset from the first electrode and laterally-adjustable along the length of the first band; and a third electrode mounted to the second band and laterally-adjustable along the length of the second band.

6 Claims, 6 Drawing Sheets

Related U.S. Application Data

(60) Provisional application No. 62/429,546, filed on Dec. 2, 2016.

(58) Field of Classification Search
USPC .......................................... 600/383, 544–545
See application file for complete search history.

(56) References Cited

U.S. PATENT DOCUMENTS

| | | | | |
|---|---|---|---|---|
| 4,683,892 A | * | 8/1987 | Johansson | A61B 5/291 600/383 |
| 6,757,556 B2 | * | 6/2004 | Gopinathan | A61B 5/0002 600/372 |
| 9,050,451 B2 | * | 6/2015 | Van Der Beek | A61B 5/0456 |
| 2007/0225585 A1 | * | 9/2007 | Washbon | A61B 5/6803 600/393 |
| 2009/0105576 A1 | * | 4/2009 | Do | A61B 5/0478 600/382 |
| 2012/0143020 A1 | * | 6/2012 | Bordoley | A61B 5/1114 600/301 |
| 2014/0051044 A1 | * | 2/2014 | Badower | A61B 5/6803 434/236 |
| 2014/0276183 A1 | * | 9/2014 | Badower | A61B 5/6803 600/544 |
| 2015/0005608 A1 | * | 1/2015 | Evans | A61B 5/0478 600/383 |
| 2015/0126846 A1 | * | 5/2015 | Jia | A61N 1/0472 600/386 |
| 2016/0066846 A1 | * | 3/2016 | Scott | A61B 5/683 600/386 |

\* cited by examiner

ELECTROENCEPHALOGRAPHY HEADSET AND SYSTEM FOR COLLECTING BIOSIGNAL DATA

CROSS-REFERENCE TO RELATED APPLICATIONS

This Application is a continuation of U.S. patent application Ser. No. 15/831,143, filed on 4 Dec. 2017, which claims the benefit of U.S. Provisional Application No. 62/429,546, filed on 2 Dec. 2016, each of which is incorporated in its entirety by this reference.

This application is related to U.S. patent application Ser. No. 15/351,016, filed on 14 Nov. 2016, which is incorporated in its entirety by this reference.

TECHNICAL FIELD

This invention relates generally to the field of electroencephalography and more specifically to a new and useful electroencephalography headset in the field of electroencephalography.

DESCRIPTION OF THE EMBODIMENTS

Figure 1:
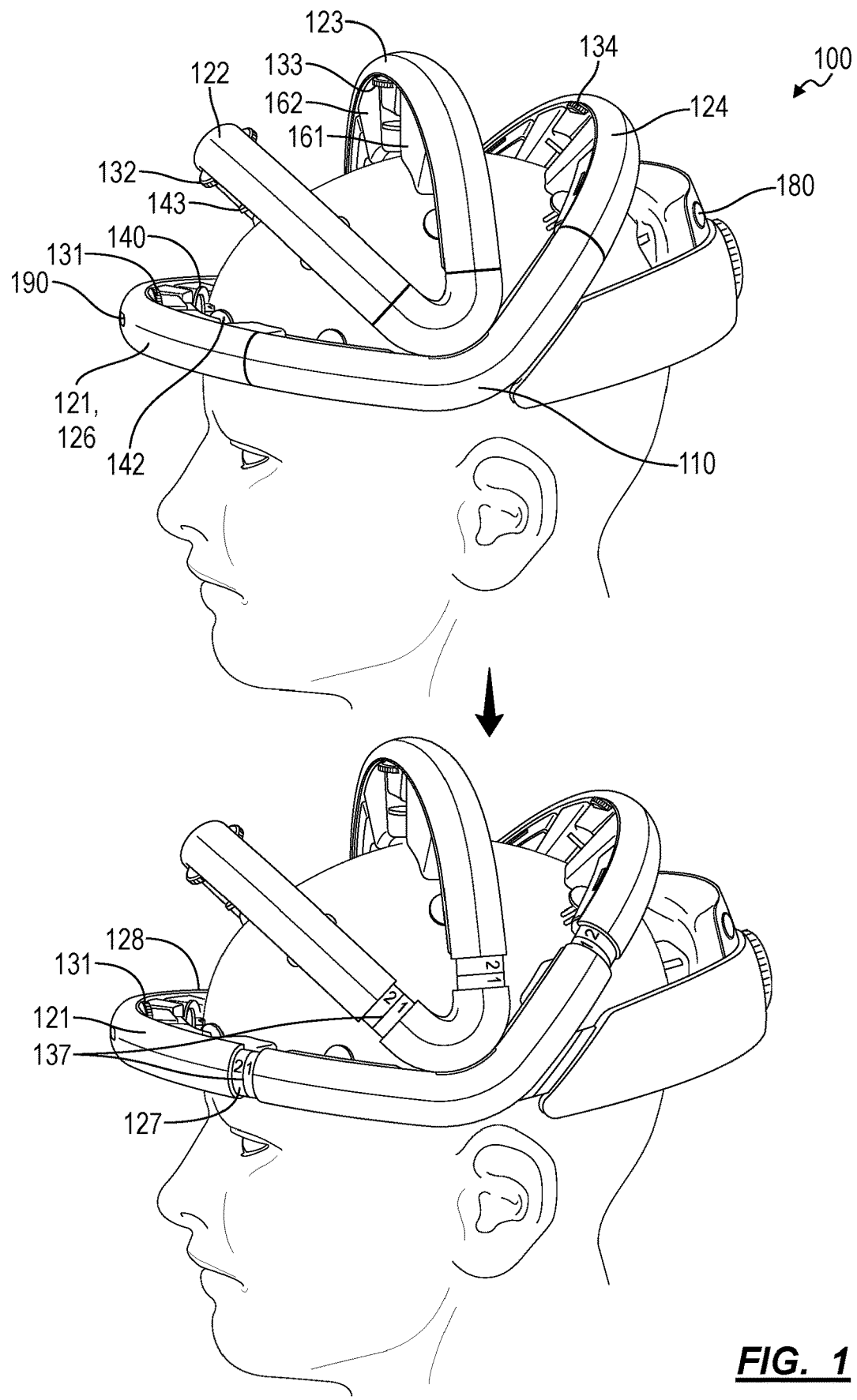
FIG. 1 is a flowchart representation of an electroencephalography (or "EEG") headset.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

As shown in FIGS. 1-8, a system for collecting biosignal data includes: a left junction 110; a right junction 112; a first band 121 spanning the left junction 110 and the right junction 112; a first band adjuster 131 configured to adjust a first length of the first band 121 between the left junction 110 and the right junction 112; a second band 122 spanning the left junction 110 and the right junction 112 and radially offset from the first band 121 about a lateral axis spanning the left junction 110 and the right junction 112; a second band adjuster 132 configured to adjust a second length of the second band 122 between the left junction 110 and the right junction 112; a first electrode 140 fixedly mounted to the first band 121 and centered between the left junction 110 and the right junction 112; a second electrode 152 mounted to the first band 121 between the first electrode 140 and the left junction 110 and laterally-adjustable along the first length of the first band 121; and a third electrode 153 mounted to the second band 122 between the left junction 110 and the right junction 112 and laterally-adjustable along the second length of the second band 122.

Figure 9:
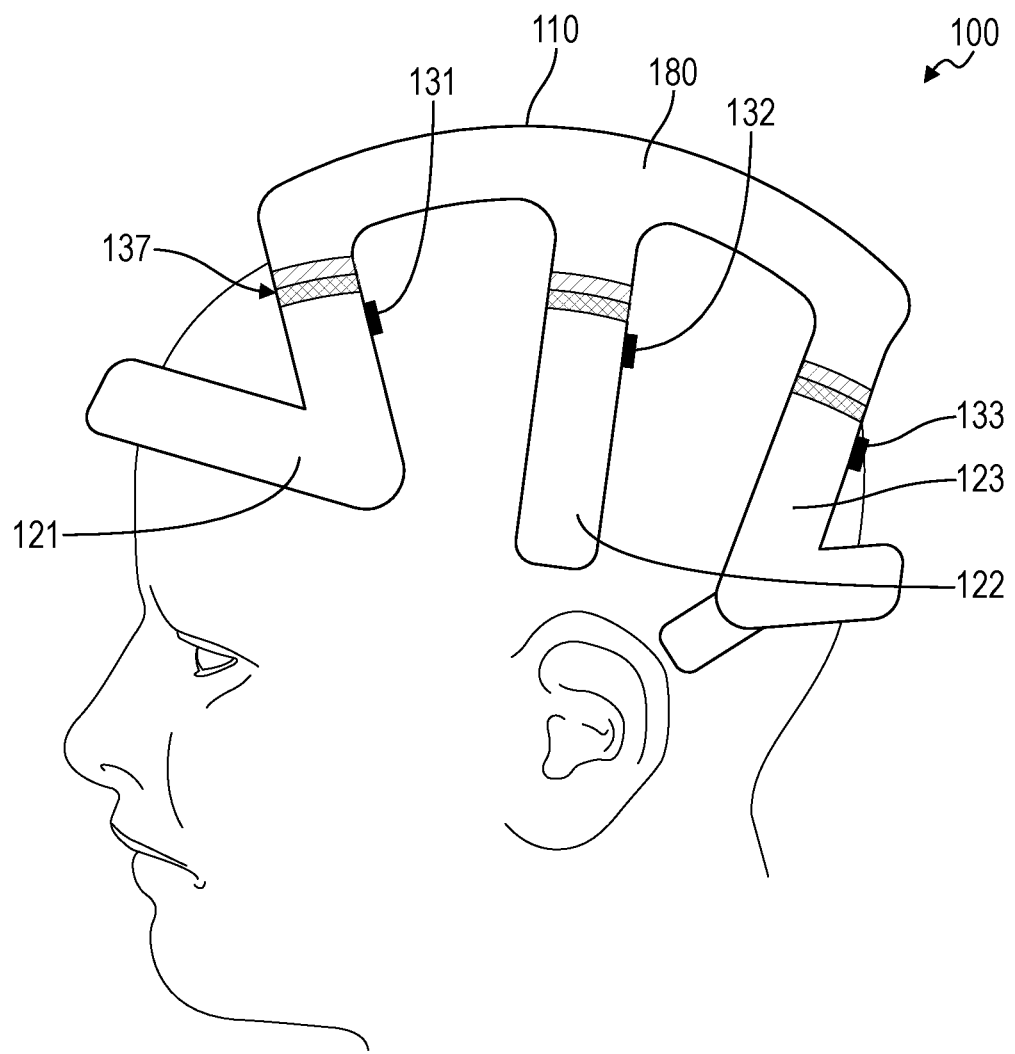
FIG. 9 is a schematic representation of one variation of the EEG headset.

One variation of the system shown in FIGS. 1 and 9 defines an electroencephalography (or "EEG") headset and includes: a junction; a first band 121 coupled to the junction; a first band adjuster 131 configured to adjust a first length of the first band 121 extending from the junction; a first length scale 137 arranged on the first band 121 and configured to indicate a particular length value, along the length scale 137, corresponding to a current length setting of the first band 121; a second band 122 coupled to the junction and radially offset from the first band 121 about a lateral axis of the junction; a second band adjuster 132 configured to adjust a second length of the second band 122 extending from the junction; a first electrode 140; a first electrode adjuster 141 coupling the first electrode 140 to the first band 121 over a range of lateral positions along the first length of the first band 121 and including a set of electrode position labels 147 indicating discrete lateral positions of the first electrode 140 in the first electrode adjuster 141, each electrode position label, in the set of electrode position labels 147, indicating a target lateral position of the first electrode 140 in the first electrode adjuster 141 for a particular length value, along the length scale 137, indicated by the first band 121 according to an electrode placement standard; and a second electrode 152 mounted to the second band 122 offset from the junction.

Figure 2:
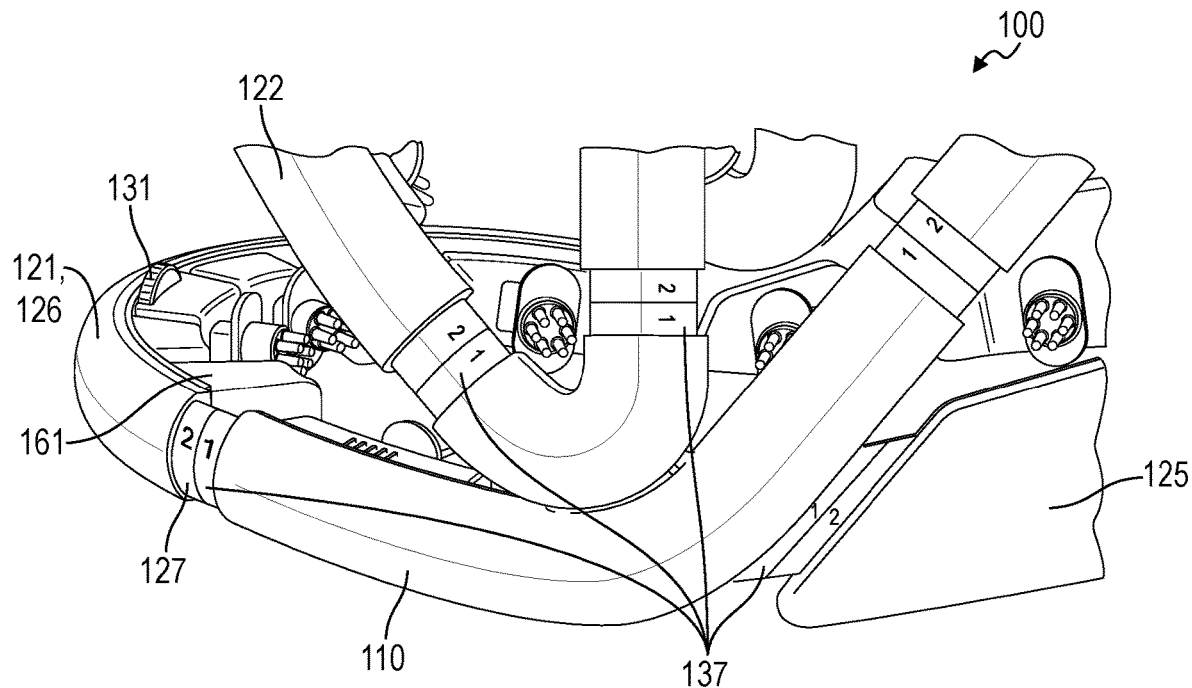
FIG. 2 is a schematic representation of one variation of the EEG headset.

As shown in FIGS. 1 and 2, another variation of the EEG headset 100 includes: a left junction 110; a right junction 112; a first band 121 adjustably coupled to and spanning the left junction 110 and the right junction 112; a first set of electrodes arranged along the first band 121; a second band 122 adjustably coupled to and spanning the left junction 110 and the right junction 112 and radially offset from the first band 121; a second set of electrodes arranged along the second band 122, the second set of electrodes including a second electrode 152 fixedly coupled to the second band 122 and centered between the left junction 110 and the right junction 112; a third band 123 adjustably coupled to and spanning the left junction 110 and the right junction 112 and radially offset from the second band 122; a third set of electrodes arranged along the third band 123, the third set of electrodes including a third electrode 153 fixedly coupled to the third band 123 and centered between the left junction 110 and the right junction 112; a fourth band 124 adjustably coupled to and spanning the left junction 110 and the right junction 112 and radially offset from the third band 123; and a fourth set of electrodes arranged along the fourth band 124, the fourth set of electrodes including a fourth electrode 154 fixedly coupled to the fourth band 124 and centered between the left junction 110 and the right junction 112

Figure 3:
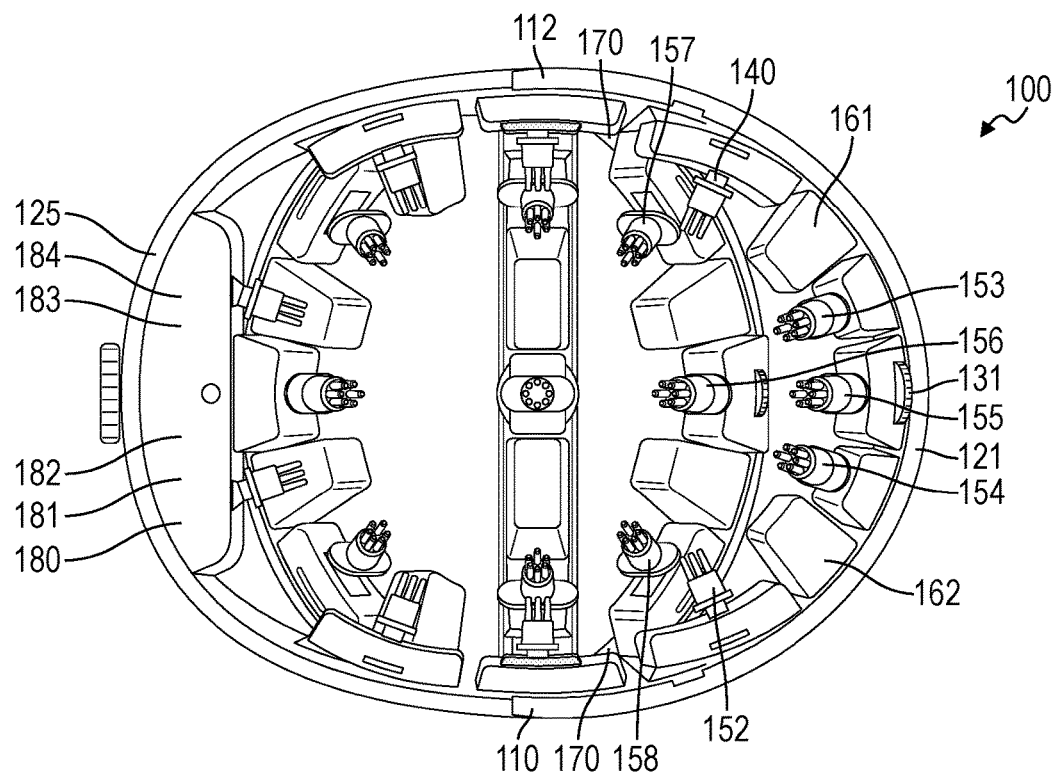
FIG. 3 is a schematic representation of one variation of the EEG headset.

As shown in FIGS. 2 and 3, yet another variation of the EEG headset 100 includes: a left junction 110 configured for placement adjacent a left ear of a user; a right junction 112 configured for placement adjacent a right ear of a user; a band 121 spanning the left junction 110 and the right junction 112; a band adjuster 131 configured to modify an effective length of the band 121 between the left junction 110 and the right junction 112; a first electrode 140 fixedly mounted to the band 121 and centered between the left junction 110 and the right junction 112; a second electrode 152; a second electrode 152 adjustor coupled to the band 121 between the first electrode 140 and the left junction 110 and supporting the second electrode 152 along a linear adjustment range; a third electrode 153; and a third electrode 153 adjustor coupled to the band 121 between the first electrode 140 and the right junction 112 and supporting the third electrode 153 along a linear adjustment range.

2. Applications

Generally, the EEG headset 100 defines a singular structure containing a set of integrated electrodes arranged across a set of adjustable bands that can be expanded and retracted to fit heads of various shapes and sizes. The set of adjustable bands are arranged in particular orientations and are configured to locate both fixed and adjustable electrodes in specific locations according to the 10-20 system (or other electrode placement standard). The set of integrated electrodes in the EEG headset 100 includes both: fixed electrodes, such as arranged at each junction and along the anteroposterior centerline of various bands; and adjustable electrodes that can be adjusted along a limited adjustment range to re-center these electrodes following adjustment of their corresponding bands. In particular, the EEG headset 100 includes mechanisms supporting both a limited number of macro adjustments at various bands and a limited number of micro adjustments at adjustable electrodes to realize electrode placement rules defined by the 10-20 system (or other electrode placement standard) within a positional tolerance of the 10-20 system.

During setup of the EEG headset 100 on a user in preparation for an EEG test, an EEG test administrator can place the EEG headset 100 on the user's head and adjust the effective length of each band via band adjusters in order to achieve a sufficiently close fit between each band and the user's scalp. Because certain electrodes within the EEG headset 100 (e.g., electrodes at the F7, F3, F4, F8, C3, C4, T5, P3, P4, and T6 positions, shown in FIGS. 3 and 6) may no longer be properly centered between adjacent fixed electrodes, the EEG test administrator can then adjust these electrodes locally via their electrode adjusters to bring the complete set of electrodes back into alignment with the 10-20 system, as shown in FIG. 7.

The junctions and bands within the EEG headset 100 can define semi-rigid structures configured to accurately and repeatably locate electrodes on a user's head according to the 10-20 system (or other electrode placement standard). Furthermore, each electrode can be integrated into and irremovable from the EEG headset 100 (except for electrode tips, which may be replaceable, as described below) such that sense signals read from each electrode during an EEG test can be automatically tagged—by the EEG headset 100 or connected computing device—with a correct channel label based on predefined locations of each electrode within the EEG. In particular, the EEG headset 100 can include a set of junctions, bands, band adjusters, electrodes, and electrode adjusters that cooperate to define a system that can be relatively quickly reconfigured for a new user by an EEG test administrator (or by the user, etc.) to accurately and repeatably realize the 10-20 system (or any other EEG system), thereby enabling the EEG headset 100 to collect quality and properly-labeled EEG data during an EEG test.

3. Junctions, Bands, and Band Adjusters

The EEG headset 100 includes: a left junction 110; a right junction 112; a first band 121 including a first end coupled to the left junction 110, a second end coupled to the right junction 112, a first band adjuster 131 configured to adjust a distance between the first end and the left junction 110 and between the second end and the right junction 112; and a second band 122 radially offset from the first band 121 and including a third end coupled to the left junction 110, a fourth end coupled to the right junction 112, and a second band adjuster 132 configured to adjust a distance between the third end and the left junction 110 and between the fourth end and the right junction 112. Generally, the left and right junctions 110, 112 function to radially locate each band (e.g., the first, second, third, fourth, and fifth bands) in the EEG headset 100, and the bands function to support fixed and adjustable electrodes against a user's scalp according to electrode placement definitions and tolerance defined by the 10-20 EEG electrode configuration (or other EEG electrode placement standard).

2.1 Junctions

The left and right junctions 110, 112 can rest on a user's head just above and in front of the user's left and right ears, respectively, and can locate: the first band 121 at a 0° position; the second band 122 at a 40° position; the third band 123 at an 80° position; the fourth band 124 at a 125° position; and the fifth band 125 at the 170° position. In this implementation, when the EEG headset 100 is worn by a user, the left and right junctions 110, 112 can thus radially locate these bands such that: the first band 121 extends across the user's forehead; the second band 122 passes over the user's frontal lobe; the third band 123 passes over the user's primary motor and somatosensory cortexes near the central sulcus; the fourth band 124 passes over the user's parietal lobe; and the fifth band 125 extends across the back of the user's skull adjacent the user's occipital lobe according to the 10-20 system.

For example, and as shown in FIG. 1, the left junction 110, the right junction 112, the first band 121, the first band adjuster 131, the second band 122, the second band adjuster 132, the first electrode 140, the second electrode 152, and the third electrode 153, etc. can cooperate to define an adjustable EEG headset configured to be worn on a head of a user. The left junction 110 can be configured to fall adjacent a left ear of the user when the adjustable EEG headset is worn on the head of the user; and the right junction 112 can be configured to fall adjacent a right ear of the user when the adjustable EEG headset is worn on the head of the user. The third band 123 can extend approximately along a coronal plane over the head of the user when the adjustable EEG headset is worn on the head of the user; and the second band 122 can extend over the head of the user between the third band 123 and a forehead of the user when the adjustable EEG headset is worn on the head of the user.

3.2 Band Adjustment

In one implementation shown in FIGS. 1 and 2, a band 121 includes: a left strap defining a left internal rack 127 (or "toothed strap") and extending from the left junction 110; a right strap defining a right internal rack 128 and extending from the right junction 112; and a sleeve 126 enclosing the left internal rack 127 and the right internal rack 128. In this implementation, the electrodes can be coupled to the sleeve 126; a band adjuster 131 for this band can include a gear arranged on the sleeve 126, engaged to the left internal rack 127 relative to the right internal rack 128, manually operable in a first direction to expand the first band 121, and manually operable in a second direction to contract the first band 121.

For example, a first band 121 extending toward the front of the EEG headset 100 (e.g., configured to fall along, contact, or otherwise engage a user's forehead) can include: a left strap extending from the left junction 110 toward the front of the EEG headset 100 and defining a left rack gear 127; and the right strap extending from the right junction 112 toward the front of the EEG headset 100, vertically offset from the left strap, curving toward and overlapping the left strap, and defining a right rack gear 128 facing the left rack gear 127. In this implementation, the first band 121 also includes a sleeve 126 that spans the left and right junctions 110, 112 and encases the left and right rack gears 127, 128. In this example, a first band adjuster 131 can include: a knurled knob arranged over or extending outside of the sleeve 126; and a pinion arranged inside the sleeve 126, interposed between and mating with the left and right rack gears 127, 128 and radially coupled to the knob. Thus, when the EEG test administrator rotates the knob in a first direction, the pinion can drive the left and right rack gears 127, 128 apart, thereby increasing the effective length of the first band 121. Similarly, when an EEG test administrator rotates the knob in a second direction, the pinion can drive the left and right rack gears 127, 128 toward each other, thereby shortening the effective length of the first band 121. In particular, rotation of the band adjuster 131 can uniformly shift the first and second ends of the first band 121 away from (or toward) the left and right junctions 110, 112, respectively. Furthermore, surfaces on the left and right straps extending from the left and right junctions 110, 112 can also include demarcations—such as printed, embossed, or debossed alphabetic or numerical symbols in the form of a scale—that are exposed as the first band 121 is expanded, thereby visually indicating the adjustment position of the first band 121.

In this implementation, the first band 121 can also include a length scale 137 corresponding to discrete lengths (or discrete length sub-ranges) of the first band 121, wherein each length value along the length scale 137 corresponds to a particular electrode position label—in a set of electrode position labels 147—on a linear rack that couples an adjustable electrode to the first band 121, as described below, as shown in FIG. 2. The first band 121 (and/or the first band adjuster 131) can thus indicate a particular length value—along this length scale 137—that corresponds to a current length setting of the first band 121 as a technician or EEG test administrator adjusts the EEG headset 100 for the unique size and shape of a user's head. For example: the length scale 137 can include discrete textual symbols highlighted in a range of discrete colors arranged on the left internal rack 127; and the sleeve 126 can indicate a particular textual symbol, in the first sequence of discrete textual symbols, corresponding to a current length setting of the first band 121 by obscuring all textual symbols other than the particular textual symbol corresponding to the current length of the first band 121 or by aligning a pointer to this particular textual symbol. As described below, the technician or EEG test administrator can then manually shift adjustable electrodes on the first band 121 to lateral positions labeled with the same textual symbol and/or color value in order to locate these adjustable electrodes within a threshold locational tolerance of their target locations on the user's scalp—relative to each other, relative to a fixed electrode on the first band 121, and/or relative to electrodes on other bands in the EEG headset 100, etc.—specified by a 10-20 EEG electrode configuration or (other electrode placement standard). The technician or EEG test administrator can repeat this process for each other band and adjustable electrode in the EEG headset 100 in order to configure the EEG headset 100 for the user.

In the foregoing implementation, each other band in the EEG headset 100 can similarly include a left strap 127, and right strap 128, a sleeve 126, and a band adjuster 131 configured to expand and contract the band 121 when manipulated by an EEG test administrator. These left straps can terminate at the left junction 110, and these right straps can terminate at the right junction 112. The left and right junctions 110, 112 can therefore form reference locations on a user's head (e.g., above and immediately ahead of the user's ears) and can radially locate the bands (e.g., the first, second, third, fourth, and fifth bands) relative to one another and relative to these reference locations such that—once the bands are adjusted to length and the adjustable electrodes positioned accordingly—the set of sense electrodes within the EEG headset 100 fall within threshold distances of target electrode positions specified in the 10-20 EEG electrode configuration (or other electrode placement standard).

In another implementation shown in FIG. 9, the EEG headset 100 includes: a central body configured for placement on the top of a user's head along the anteroposterior centerline of the user's skull; a set of adjustable bands extending downwardly from the central body; and a set of fixed electrodes and adjustable electrodes distributed across the interior surfaces of the bands and the central body. In this implementation, each band can be independently adjustable and can include at least one electrode (e.g., one fixed electrode or one fixed electrode and one adjustable electrode). Alternatively, pairs of like left and right bands can be linked by a common band adjuster such that pairs of like bands are uniformly adjusted relative to the centerline of the central body.

In the foregoing implementations, the left junction 110, right junction 112, bands, and band adjusters, etc. can be formed in a rigid material, such as injection-molded plastic (e.g., nylon) or molded fiber-impregnated polymer. However, the junctions, bands, and/or central body, etc. can be formed in any other material or define any other geometry.

3.3 Chin Strap

In one variation, the EEG headset 100 further includes a chin strap coupled to the left and right junctions (or to one or more bands) and configured to fix the EEG headset 100 to a user's chin, ears, or other head feature, thereby preventing the EEG headset 100 moving relative to the user's head and from falling off of the user's head if the user moves during an EEG test performed with the EEG headset 100.

4. Sense Electrodes

The EEG headset 100 includes a set of sense electrodes arranged across the set of bands. When the EEG headset 100 is worn by the user, a sense electrode can: contact the user's scalp; detect a high-impedance sense signal from the user's skin; convert the low-amplitude, high-impedance sense signal into a well-driven low-impedance sense signal; and pass the low-impedance sense signal to the controller 184.

4.1 Electrode Composition

Each sense electrode is configured to contact a user's skin and to pass neural oscillation data in the form of a sense signal from the user's skin to the controller 184 (e.g., to a signal processor within the controller 184). For example, each sense electrode in the set of sense electrodes can define a dry EEG electrode including: a substrate; a set of electrically-conductive prongs extending from a first side of the substrate; and an amplifier coupled to the substrate opposite the set of prongs and configured to amplify an electrical signal passing through the set of prongs. The electrically-conductive prongs can be elastic (e.g., gold-plated silicone bristles) or rigid (e.g., gold-plated copper prongs). A sense electrode can alternatively include a flat or domed contact disk configured to contact the user's skin.

Figure 4:
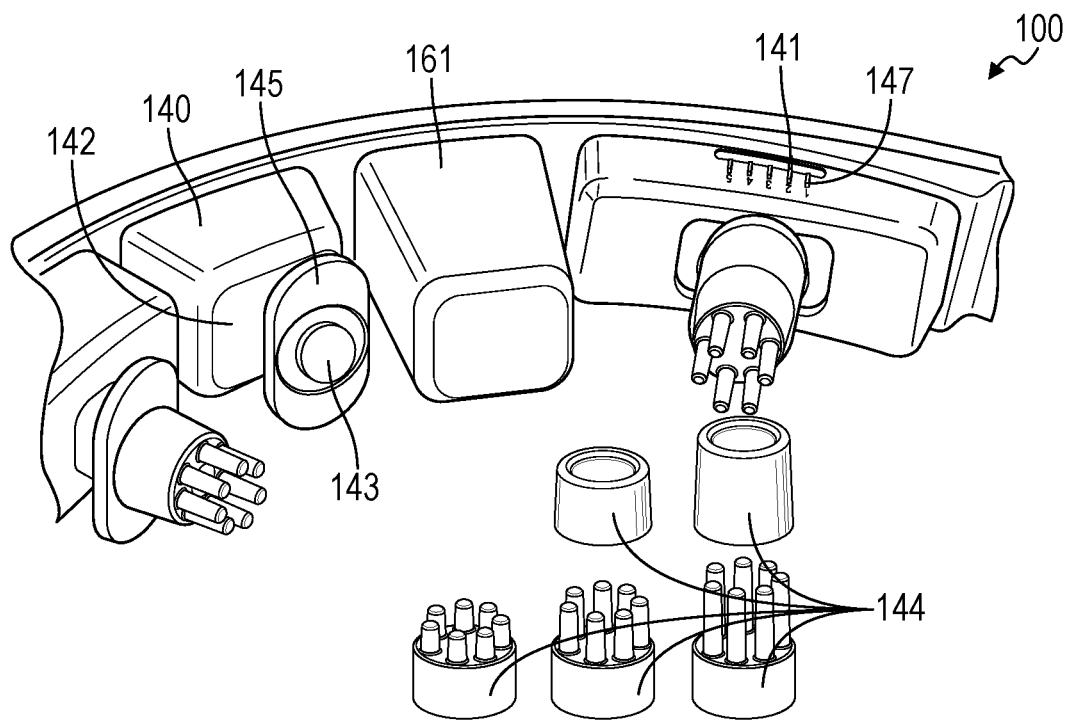
FIG. 4 is a schematic representation of one variation of the EEG headset.

As shown in FIG. 4, the sense electrode can also be configured to accept interchangeable electrode tips 144, such as one of an elastic bristle electrode tip, a rigid prong electrode tip, a flat contact disk electrode tip, and a domed contact disk electrode tip, as described below. In one implementation, each sense electrode can include: an electrode body 142 coupled to the band 121 (e.g., via an electrode adjuster 141, such as in the form of a linear rack, for adjustable electrodes); a magnetic element 143 arranged on a distal end of the electrode body 142 and including a conductive surface; and a conductive lead 146 coupled to a face of the magnetic element 143, passing through the electrode body 142, and terminating at an amplifier electrically coupled to the controller 184, such as arranged in the control module 180 described below. In this implementation, the EEG headset 100 can be supplied with a kit of electrode tips 144, wherein each electrode tip in the kit of electrode tips 144 includes a ferrous element 148 configured to transiently magnetically couple to the magnetic element 143 and to transiently electrically couple to the conductive lead 146 via the conductive surface of the magnetic element 143. In this implementation, a hard or soft contact surface on an electrode tip can electrically couple to the ferrous element 148 on the back side of the electrode tip; the magnetic element 143 can include an electrically-conductive surface (e.g., chrome or tin plating); and the amplifier—such as arranged inside the electrode body 142 or nearby in the adjacent band—can electrically couple to the magnetic element 143 via a wire arranged inside of the electrode body 142. When an electrode tip is thus installed on an electrode, the ferrous element 148 in the electrode tip can directly contact the magnetic element 143, thereby electrically coupling the contact surface of the electrode tip 144 to the amplifier. For example, a first end of the conductive lead 146 can be bonded to (e.g., potted around) a face of the magnetic element 143 with (conductive) adhesive, compressed against the face of the magnetic element 143 with a spring arranged inside the electrode body 142, or connected to a spring loaded pin in contact with the face of the magnetic element 143. A separate conductive lead 146 connected to an output of the amplifier can pass through the band 121 and connect to an input of the controller 184.

In the foregoing implementation, the kit of electrode tips 144 can include electrode tips 144 defining different constant surfaces, such as one each of a hard domed electrode surface, a hard pronged electrode surface, and a soft domed electrode surface. Electrodes in the kit can also define various lengths, such as matched to lengths of support blocks installed on adjacent regions of a band 121, as described below and shown in FIG. 4, such as to enable an EEG test administrator to reconfigure the EEG headset 100 for both adult and juvenile users.

4.2 Adjustable and Fixed Electrode Layout

As shown in FIGS. 3 and 4, the EEG headset 100 can include electrodes mounted to the interior surfaces of corresponding bands via electrode adjusters (hereinafter "adjustable electrodes") at select locations (e.g., at other than the lateral centerline of the EEG headset 100, the immediate front and rear of the EEG headset 100, and the lateral extents of the EEG headset 100). The EEG headset 100 can also include electrodes fixedly coupled to the interior surfaces of corresponding bands (hereinafter "fixed electrodes") at other locations.

Figure 6:
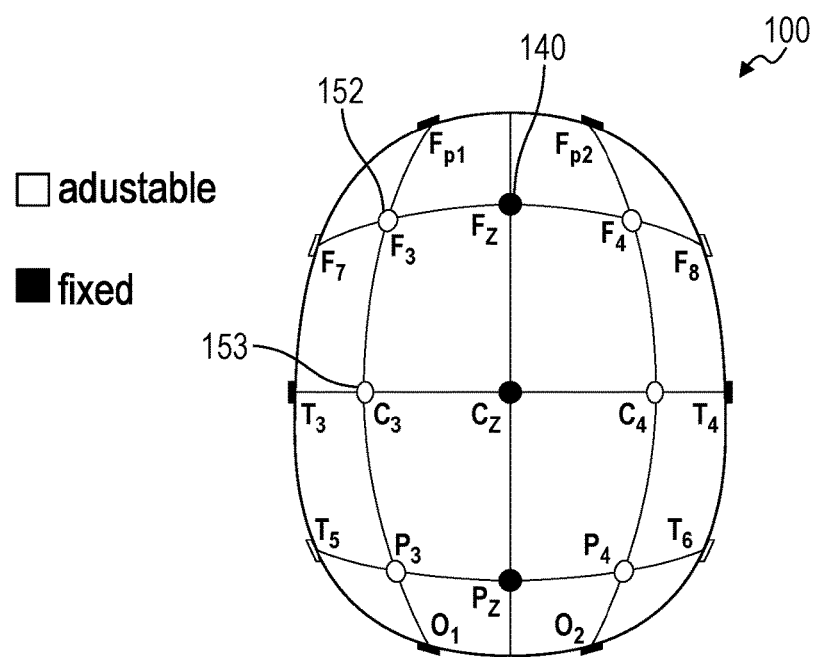
FIG. 6 is a schematic representation of one variation of the EEG headset.
Figure 7:
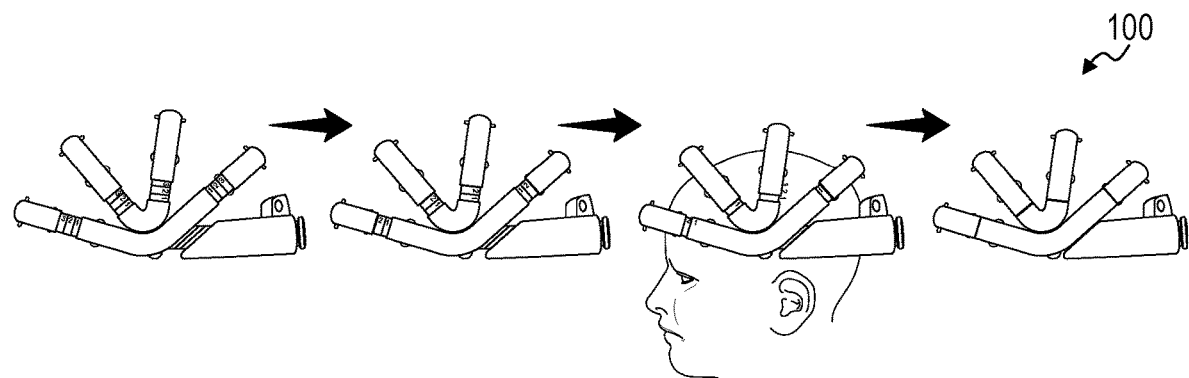
FIG. 7 is a flowchart representation of one variation of the EEG headset.

In one implementation: the EEG headset 100 includes nineteen sense electrodes in a combination of fixed and adjustable configurations arranged across the set of bands, including one sense electrode for each of: the F7, Fp1, Fp2, and F8 positions (defined in the 10-20 system) along the first band 121; the F3, Fz, and F4 positions along the second band 122; the T4 position at the right junction 112; the T3 position at the left junction 110; the C3, Cz, and C4 positions along the third band 123; the P3, Pz, and P4 positions along the fourth band 124; and the T5, O1, O2, and T6 positions along the fifth band 125, as shown in FIGS. 3 and 6. In particular, in this example: the first band 121 can include fixed sense electrodes at the Fp1 and Fp2 sense electrode positions and adjustable sense electrodes at the F7 and F8 sense electrode positions; the second band 122 can include a fixed sense electrode at the Fz sense electrode position and adjustable sense electrodes at the F3 and F4 sense electrode positions; the third band 123 can include a fixed sense electrode at the Cz sense electrode position and adjustable sense electrodes at the C3 and C4 sense electrode positions; the fourth band 124 can include a fixed sense electrode at the Pz sense electrode position and adjustable sense electrodes at the P3 and P4 sense electrode positions; and the fifth band 125 can include fixed sense electrodes at the T5 and T6 sense electrode positions and adjustable (or fixed) sense electrodes at the O1 and O2 sense electrode positions. The EEG headset 100 can also include fixed sense electrodes at the T4 sense electrode position at the right junction 112 and at the T3 sense electrode position at the left junction 110, as shown in FIG. 6. The EEG headset 100 can further include a fixed drive electrode fixedly mounted to the first band 121 between the FP1 and FP2 sensor electrode positions, centered between the left junction 110 and the right junction 112, and configured to contact a user's skin proximal the user's forehead (e.g., centered just above the bridge of the user's nose).

In particular, in addition to the first band 121 and the second band 122, the EEG headset 100 can include: a third band 123 spanning the left junction 110 and the right junction 112 and supporting a laterally-adjustable C3 electrode, a fixed Cz electrode, and a laterally-adjustable C4 electrode in the 10-20 EEG electrode configuration; a third band adjuster 133 configured to adjust a length of the third band 123 between the left junction 110 and the right junction 112; a fourth band 124 spanning the left junction 110 and the right junction 112 and supporting a laterally-adjustable P3 electrode, a fixed Pz electrode, and a laterally-adjustable P4 electrode in the 10-20 EEG electrode configuration; a fourth band adjuster 134 configured to adjust a length of the fourth band 124 between the left junction 110 and the right junction 112; and a fifth band 125 spanning the left junction 110 and the right junction 112 and supporting a laterally-adjustable T5 electrode, a fixed O1 electrode, a fixed O2 electrode, and a laterally-adjustable T6 electrode in the 10-20 EEG electrode configuration, as shown in FIGS. 1, 3, and 6.

Therefore, in the foregoing example: a first electrode 140 mounted to the first band 121 can define a laterally-adjustable F7 electrode; a second electrode 152 mounted to the first band 121 between the first electrode 140 and the right junction 112 can be laterally-adjustable along the first length of the first band 121 to define a laterally-adjustable F8 electrode; a third electrode 153 fixedly mounted to the first band 121 between the first electrode 140 and the second electrode 152 can define a fixed FP1 electrode; a fourth electrode 154 fixedly mounted to the first band 121 between the second electrode 152 and the third electrode 153 can define a fixed FP2 electrode; a fifth electrode 155 fixedly mounted to the first band 121 between the third electrode 153 and the fourth electrode 154 (e.g., centered between the left junction 110 and the right junction 112) can define a fixed drive electrode; a sixth electrode 156 mounted at the lateral centerline of the second band 122 can define a fixed Fz electrode; a seventh electrode 157 mounted to the second band 122 between the sixth electrode 156 and the left junction 110 can define a laterally-adjustable F3 electrode; and an eighth electrode 158 mounted to the second band 122 between the sixth electrode 156 and the right junction 112 can be laterally-adjustable along the second length of the second band 122 to define a laterally-adjustable F4 electrode in the 10-20 EEG electrode configuration; etc.

Furthermore, each band adjuster can be configured to expand its corresponding band equally between the left junction 110 and the right junction 112 in order to maintain certain fixed electrodes along the lateral centerline of the EEG headset 100. For example, the second band 122 can include a fixed electrode in the Fz position, and the second band adjuster 132 can be configured to expand the second band 122 equally between the left junction 110 and the right junction 112 in order to maintain the Fz electrode along the lateral centerline of the EEG headset 100. Similarly, the third band 123 can include a fixed electrode in the Cz position, and the third band adjuster 133 can be configured to expand the third band 123 equally between the left junction 110 and the right junction 112 in order to maintain the Cz electrode along the lateral centerline of the EEG headset 100.

4.2 Adjustable Electrode

Figure 5:
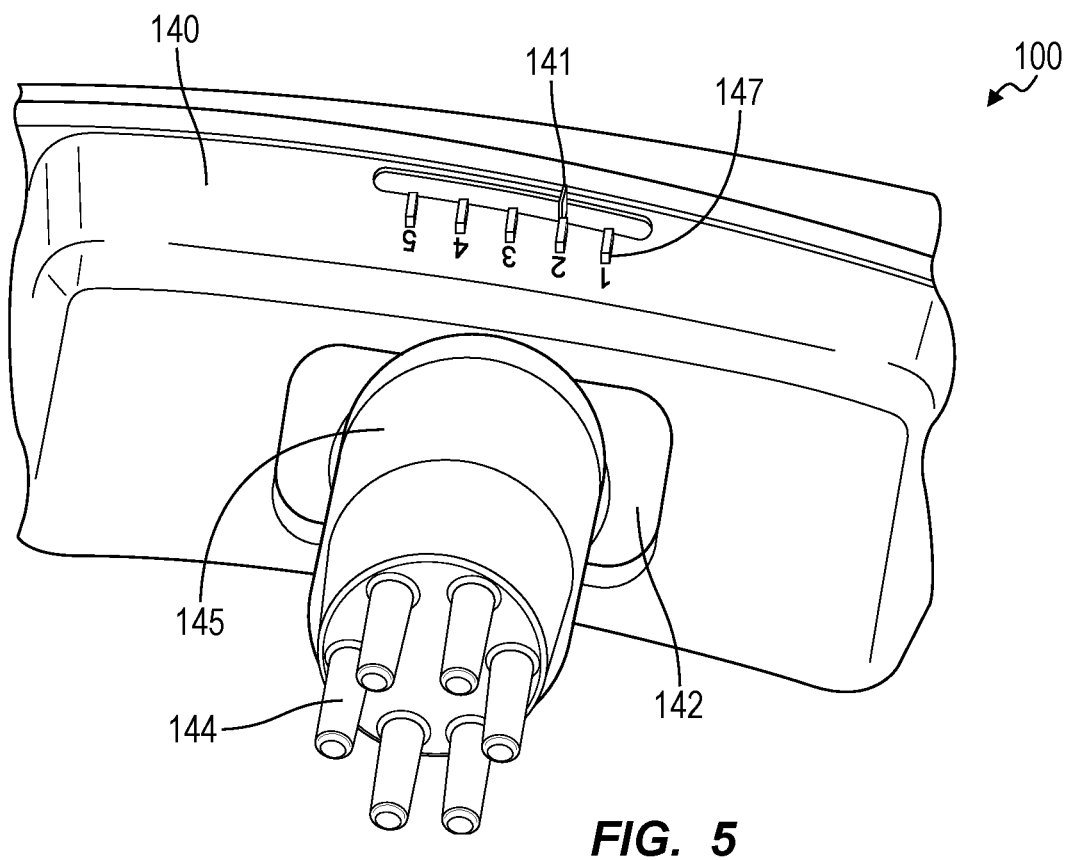
FIG. 5 is a schematic representation of one variation of the EEG headset.
Figure 8:
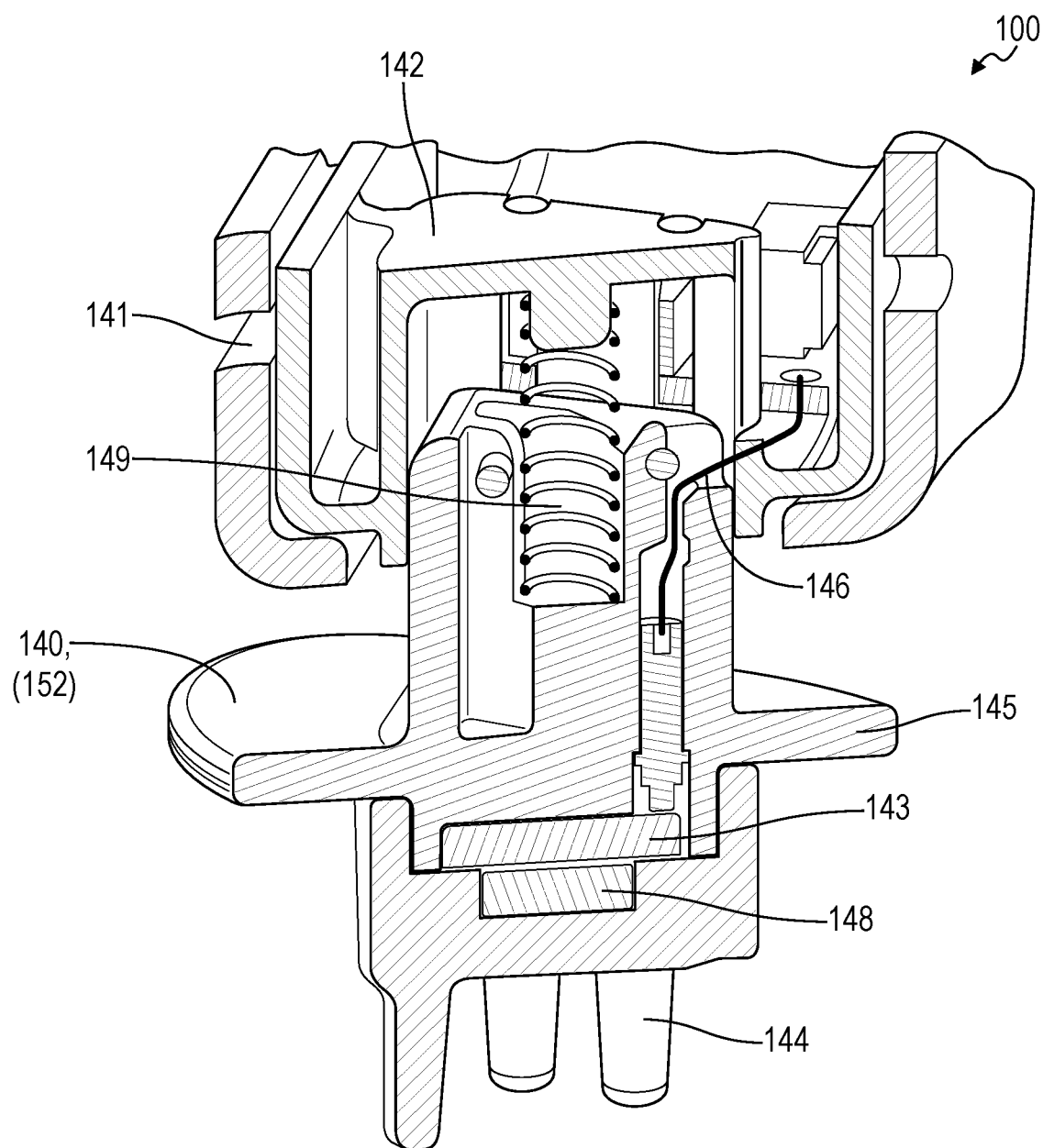
FIG. 8 is a schematic representation of one variation of the EEG headset.

In one implementation shown in FIGS. 4, 5, and 8, an adjustable electrode includes: a sense electrode; a sliding element supporting the sense electrode; a ratchet mechanism (or rack gear and follower) mounted to a band 121 and configured to retain the position of the sliding element relative to the band 121; and a button that, when manually depressed, releases the sliding element from the ratchet mechanism (or releases the follower from the rack gear), thereby enabling an EEG administrator to shift the position of the sliding element—and therefore the sense electrode—relative to the band 121. In this implementation, the sliding element and ratchet mechanism can cooperate to locate the sense electrode across a range of positions, including a linear distance parallel to the length of its corresponding band and equal to approximately half of the maximum change in effective length of the band 121 from its fully-retracted to fully-expanded positions such that the adjustable electrode can be centered between two adjacent fixed electrodes according to the 10-20 system substantially regardless of adjustment positions of the band 121. Furthermore, the band 121 supporting the adjustable electrode can include demarcations—such as printed, embossed, or debossed alphabetic or numerical symbols in the form of a scale—adjacent the button to visually indicate the adjustment position of the adjustable electrode, as shown in FIG. 5.

In a similar implementation shown in FIG. 5, an adjustable electrode includes: a sense electrode; and an electrode adjuster 141 coupling the sense electrode to a corresponding band over a range of lateral positions along the length of the band 121. For example, the electrode adjuster 141 can include a linear rack, and the sense electrode can be mounted to the linear rack via a ratchet or detent mechanism that selectively retains the sense electrode in discrete locations along the linear rack. The electrode adjuster 141 can also include a set of electrode position labels 147 (e.g., a lateral position scale) indicating discrete lateral positions of the sense electrode along the electrode adjuster 141, wherein each electrode position label—in this set of electrode position labels 147—indicates a target lateral position of the sense electrode along the electrode adjuster 141 for a particular length value—along the length scale 137—indicated by the band 121, as described above, according to an electrode placement standard (e.g., a 10-20 EEG electrode configuration). In particular, the band 121 can include a length scale 137 corresponding to discrete lengths of the band 121, wherein each length value along the length scale 137 indicates correspondence to a particular electrode position label in the set of electrode position labels 147 on the linear rack. As described above, the band 121 can indicate a particular length value—along the length scale 137—corresponding to a current length setting of the band 121, and an EEG test administrator can adjust the sense electrode along the linear rack to match the electrode position label indicated by the sense electrode to the particular length value indicated by the band 121 in order to locate the sense electrode within a threshold tolerance of its target position relative to another sense electrode in the EEG headset 100.

For example, the length scale 137 on the band 121 can include a first sequence of discrete textual symbols highlighted in a range of discrete colors arranged on the left internal rack 127, as shown in FIG. 2; the adjustable electrode can be assigned a target location relative to another electrode (e.g., a fixed electrode arranged along the lateral centerline of the EEG headset 100) on the band 121 according to a 10-20 EEG electrode configuration; and the set of electrode position labels 147 on the linear rack can include a second sequence of discrete textual symbols highlighted in the range of discrete colors and arranged along the linear rack, as shown in FIG. 5, wherein each textual symbol in the second sequence of discrete textual symbols indicates a target lateral position of the second electrode 152 along the linear rack for a corresponding textual symbol—in the first sequence of discrete textual symbols—indicated by the band 121. Each adjustable band and each other adjustable electrode on each adjustable band can be similarly annotated with length scales and electrode position labels 147, respectively, to assist an EEG test administrator in rapidly adjusting the EEG headset 100 to a user's unique head geometry by: adjusting the bands to fit the user's head; and then shifting each sense electrode in its linear rack to match its electrode position label to the length value of its corresponding band.

4.4 Junction Electrodes

In one variation shown in FIGS. 1 and 3, the left junction 110 is configured for placement adjacent a left ear of the user, and the right junction 112 is laterally offset from the left junction 110 and configured for placement adjacent a right ear of the user when the adjustable EEG headset is worn on the head of the user. In this variation, a T3 electrode can be fixedly mounted to the left junction 110, and a T4 electrode can be fixedly mounted to the right junction 112.

Because the geometry of the left and right junctions 110, 112 and the user's ears and hair near the left and right junctions 110, 112 may visually obstruct these T3 and T4 electrodes and thus inhibit an EEG test administrator from easily observing contact between these electrodes and the user's scalp, the EEG headset 100 can also include: a left light element 170 adjacent the T3 electrode, facing inwardly from the left junction 110 toward the right junction 112, and configured to illuminate the T3 electrode adjacent a scalp of the user when the adjustable EEG headset is worn on the head of the user; and a right light element 170 adjacent the T4 electrode, facing inwardly from the right junction 112 toward the left junction 110, and configured to illuminate the T4 electrode adjacent the scalp of the user when the adjustable EEG headset is worn on the head of the user, as shown in FIG. 3. The EEG headset 100 (e.g., the controller 184) can therefore activate the left and right light elements 170 during a setup period preceding an EEG test and/or throughout the EEG test in order to illuminate the T3 and T4 electrodes, thereby better enabling the EEG test administrator to quickly visually observe these electrodes and make adjustments to these electrodes or to the band 121 to improve contact with the user's scalp.

4.5 Support Blocks

Each adjustable electrode (and each fixed electrode) can also include a spring element 149 between the sense electrode and the sliding element and configured to depress the electrode toward a user's head and to absorb variations in distances between the band 121 and users' scalps when the EEG headset 100 is worn by a variety of users.

In one implementation shown in FIGS. 2, 3, and 4, the EEG headset 100 further includes support blocks: arranged on each side of electrodes on the bands; configured to elevate the bands off of the scalp of the user and thus improve manual access to electrodes facing inwardly from these bands; and to rest on the head of a user and thus distribute the weight of EEG headset 100 on the user's head, which may be more comfortable for a user than smaller electrodes (such as with pronged tips) carrying the weight of the EEG headset 100 into the user's scalp. For example, the EEG headset 100 can include: a first support block 161 arranged on the first band 121 between the first electrode 140 and the second electrode 152, extending toward a median of a lateral axis coinciding with the left junction 110 and the right junction 112, and defining a first surface facing the lateral axis and configured to rest against a head of a user; and a second support block 162 arranged on the first band 121 adjacent the second electrode 152 laterally opposite the first support block 161, extending toward the median of the lateral axis, and defining a second surface facing the lateral axis and configured to rest against the head of the user. In this example, the support blocks can include solid or rigid hollow structures with soft (e.g., foam, rubber) surfaces configured to contact a user's head and to cushion the weight of the EEG headset 100 on the user's head.

In this implementation, the second electrode 152 can include: an electrode body 142 coupled to the first band 121; an electrode tip 144 coupled to the electrode body 142 opposite the first band 121, as described above; and a spring element 149 arranged inside the electrode body 142 and configured to bias the electrode tip 144 past the first surface and the second surface toward the median of the lateral axis, as shown in FIG. 8. In particular, the electrode tip 144 of the second element can extend inwardly past the soft surfaces of the support blocks by a minimal distance (e.g., approximately three millimeters) at full extension, and the spring element 149 can bias the second electrode 152 to full extension. When the EEG headset 100 is placed on a user's head, the tip of the second electrode 152 can fall against the user's scalp, and the weight of the EEG headset 100 over the second electrode 152 can compress the spring element 149 in the second electrode 152, thereby collapsing the second electrode 152 until the adjacent support blocks contact the user's scalp. The spring element 149 can thus compress the electrode tip 144 of the second electrode 152 against the user's scalp with substantially consistent force (e.g., within a narrow range of target electrode tip 144 forces or pressures); and the support blocks can carry (some of) the load of the EEG headset 100 into the user's head. Because the soft surfaces of the support blocks define larger surface areas than the second electrode 152, the support blocks can thus decrease local pressures of the EEG headset 100 on the user's scalp and yield improved comfort for the user.

In this implementation, the second electrode 152 can also include a shoulder 145 adjacent the electrode tip 144, such as defining a rim extending radially about the electrode body 142 aft of and coupled to the electrode tip 144, as shown in FIGS. 5 and 8. The spring element 149 can further support manual retraction of the electrode tip 144—via the shoulder 145—past the surfaces of the adjacent support blocks toward the first band 121 in order to separate the electrode tip 144 from the head of the user during lateral adjustment of the first electrode 140 on the first band 121. In particular, rather than maintaining contact between the electrode tip 144 of the second electrode 152 and the user's scalp while moving the second electrode 152 laterally along its electrode adjuster 141, while may be uncomfortable for the user and cause the electrode tip 144 to separate from the electrode body 142, an EEG test administrator may: grip the shoulder 145 between her thumb and forefinger (with the base of the thumb adjacent the first band 121); retract the second electrode 152 toward the first band 121 to separate the electrode tip 144 from the user's scalp; draw the second electrode 152 laterally to a target position—indicated by electrode position labels 147—on the electrode adjuster 141; and then release the shoulder 145. The spring element 149 can thus drive the electrode tip 144 forward and back into contact with the user's scalp and retain the electrode tip 144 in contact with the user's scalp within the target electrode tip 144 force range.

As described above and shown in FIG. 4, the electrodes can include replaceable electrode tips 144 of various geometries. The EEG headset 100 can therefore also include a kit of support blocks of various geometries (e.g., lengths) matched to the geometries of various electrode tips 144. For example, the electrode tip 144 of the second electrode 152 can be transiently coupled to the electrode body 142 of the second electrode 152 and can be configured for installation on the electrode body 142 in combination with installation of the first support block 161 and the second support block 162 on the first band 121 such that this electrode tip 144 extends inwardly just past the inner surfaces of the first and second support blocks 161, 162 when the second electrode 152 is at full extension with this electrode tip 144 installed. In this example, the EEG headset 100 can also include: a third support block defining a height greater than the height of the first support block 161 and interchangeable with the first support block 161 on the first band 121; a fourth support block 164 defining a height greater than the height of the second support block 162 and interchangeable with the second support block 162 on the first band 121; and including a second electrode 152 tip configured to transiently couple to the electrode body 142 of the second electrode 152, interchangeable with the electrode tip 144 on the electrode body 142 of the second electrode 152; defining a length greater than the electrode tip 144; and configured for installation on the electrode body 142 in combination with installation of the third support block and the fourth support block 164 on the first band 121. In particular, the heights of the third and fourth support blocks 163, 164 can be matched to the length of the second electrode 152 tip such that the longer second electrode 152 tip extends inwardly just past the inner surfaces of the third and fourth support blocks when the second electrode 152 is at full extension with the second electrode 152 tip installed. In this example, the support blocks can be snapped, fastened, or otherwise transiently connected to support block receptacles between electrodes on the bands.

Other electrodes on the EEG headset 100 can include similar spring elements 149 and shoulders 145, and the EEG headset 100 can include similar support blocks mounted to the ends adjacent these other electrodes. However, the EEG headset 100 can include any other type and geometry of electrode tips 144 and matched support blocks of any other material or geometry.

Furthermore, the adjustable electrode can include a slotted grommet arranged between the sliding element and the sense electrode. For example, the slotted grommet can be of a compressible material (e.g., silicone foam), configured to prevent ingress of debris into the ratchet mechanism, and configured to damp motion of the sense electrode relative to the band 121 and to retain the position of the sense electrode relative to the band 121 in order to reduce noise in a sense signal read from the sense electrode during an EEG test. Each adjustable electrode (and each fixed electrode) can additionally or alternatively include a screw element that, when adjusted by an EEG test administrator, drives the entire sense electrode (or the electrode tip 144 of the sense electrode exclusively) toward or away from the band 121, thereby enabling the EEG test administrator to tune a force applied by an electrode tip 144 to an adjacent surface of the users skin and to configure the EEG headset 100 for users having heads of different shapes and geometries.

However, an adjustable electrode within the EEG headset 100 can be of any other form and can be configured in any other way to locate a sense electrode across a variety of users' heads—of different shapes and sizes—according to the 10-20 EEG electrode configuration (or other EEG electrode placement standard). The EEG headset 100 can also include any other number and type of active or passive, dry or wet sense electrodes configured to output any other low- or high-impedance signal to a signal processor or controller 184 in the EEG headset 100, as described below.

4.6 Electrode Position Feedback

In this variation, the EEG headset 100 (and/or the native EEG test application executing on an external computing device) can detect global adjustments of the EEG headset 100 at each band and local adjustments at each adjustable electrode to confirm that the position of each adjustable electrode conforms to the 10-20 system, such as within a predefined tolerance (e.g., +/−five millimeters). The EEG headset 100 (or native EEG test application hosting an EEG portal on an external computing device connected to the EEG headset 100) can serve prompts to an EEG test administrator—in real-time—to adjust certain adjustable electrodes in order to bring the EEG headset 100 into alignment with the 10-20 system prior to start of an EEG test.

In one implementation, the first band 121 includes a band 121 potentiometer interposed between the first band 121 and the left (or right) junction, wherein the internal electrical resistance of the band 121 potentiometer changes as a function of an adjusted position of the first band 121, such as a function of a distance between a first end of the first band 121 and the left junction 110. In this implementation, the EEG headset 100 also includes: an F4 electrode adjuster supporting an F4 sense electrode proximal an F7 position on the first band 121; an F8 electrode adjuster supporting an F8 sense electrode proximal an F8 position on the first band 121; an F7 electrode potentiometer coupled to the first band 121 and to the F7 electrode adjuster and exhibiting a change in internal resistance as a function of the position of the F7 electrode adjuster on the first band 121; and an F8 electrode potentiometer coupled to the first band 121 and to the F8 electrode adjuster and exhibiting a change in internal resistance as a function of the position of the F8 electrode adjuster on the first band 121.

During setup, the controller 184 can sample the band 121, F7 electrode, and F8 electrode potentiometers and then implement methods and techniques described below to calculate: a length of the first band 121 based on a voltage (or internal resistance) read from the band 121 potentiometer; a position of the F7 electrode relative to the first band 121 based on a voltage (or internal resistance) read from the F7 electrode potentiometer; and a position of the F8 electrode relative to the first band 121 based on a voltage (or internal resistance) read from the F8 electrode potentiometer, such as based on a lookup table or set of parametric equations for each of these potentiometers. The controller 184 can then calculate a target position of the F7 electrode based on the length of the first band 121, such as a singular target position (e.g., in the form of a target voltage or resistance of the first electrode 140 potentiometer) or a target voltage range (e.g., in the form of a target voltage or resistance range of the first electrode 140 potentiometer) based on predefined rules of the 10-20 system. The controller 184 can implement similar methods and techniques to calculate a target position of the F8 electrode. The controller 184 can then compare the actual positions of the F7 and F8 electrodes to the target positions or target position ranges of the F7 and F8 electrodes to confirm that the F7 and F8 electrodes fulfill rules defined by the 10-20 system.

Alternatively, the controller 184 can: access a lookup table that links a voltage (or resistance) read from the band 121 potentiometer on the first band 121 directly to a singular target potentiometer voltage for each of the F7 and F8 electrode potentiometers; calculate a difference between the singular target potentiometer voltages and actual voltages read from the F7 and F8 potentiometers; and then directly confirm alignment of the F7 and F8 electrode to the 10-20 system if these differences do not exceed a threshold voltage difference representing a tolerance of the 10-20 system.

If the controller 184 confirms that one or both of the F7 and F8 electrodes are positioned outside of an acceptable range of positions on the first band 121 necessary to realize the 10-20 system, the controller 184 can transmit a notification to correct the position of the F7 and/or F8 electrodes to an external computing device connected to the EEG headset 100, such as to a computing device executing a native EEG test application hosting the EEG portal. For example, for the EEG headset 100 that includes symbolic position indicators adjacent each adjustable electrode, as described above, the EEG headset 100 can transmit to the connected computing device a notification to correct the position of the F7 electrode, including a target positional character (e.g., "5/10" or "E") at which to set the F7 electrode adjustor if the F7 electrode is determined to be outside of its acceptable positional range. In another example, the EEG headset 100 can transmit to the computing device a notification specifying an approximate physical distance and direction to shift the F7 electrode in order to realize the 10-20 system. In these examples, upon receipt of such a notification from the EEG headset 100, the native EEG test application can render this notification on a display of the computing device. The native EEG test application can additionally or alternatively update a virtual representation of the EEG headset 100 rendered on the computing device to indicate that the F7 electrode requires adjustment, such as by highlighting the F7 electrode in a virtual representation of the EEG headset 100 and inserting a directional arrow and target offset distance to shift the F7 electrode into alignment with the 10-20 system.

The EEG headset 100 can additionally or alternatively include light elements 170 (e.g., LEDs) arranged on the bands adjacent each adjustable electrode, and the controller 184 can update the state of each light element 170 to visually indicate directly on the EEG headset 100 which adjustable electrodes require repositioning to realize the 10-20 system. For example, the EEG headset 100 can include a first multicolor LED arranged on the first band 121 adjacent one end of the adjustment range of the F7 electrode and a second multicolor LED arranged on the first band 121 adjacent the opposite end of the adjustment range of the F7 electrode. The EEG headset 100 can then update the state of one of these multicolor LEDs to output a flashing "red" light to visually indicate a need to move the F7 electrode away from this LED and toward the opposing LED. Once the F7 electrode is correctly repositioned, the EEG headset 100 can update the first and second multicolor LEDs to output "green" light to visually indicate that the F7 electrode is properly positioned. Similarly, the EEG headset 100 can include a multicolor LED adjacent each adjustable electrode, and the EEG headset 100 can trigger each LED: to output a "red" color if the position of the adjacent electrode differs significantly from a target electrode position; to output a "yellow" color if the position of the adjacent electrode is just outside acceptable bounds of a target electrode position; and to output a "green" color if the position of the adjacent electrode is within acceptable bounds of a target electrode position.

The system can include similar arrangements of electrode potentiometers at other adjustable electrodes in the EEG headset 100, and the EEG headset 100 (and/or the native EEG test application executing on the connected computing device) can implement similar methods and techniques to confirm that the position of each adjustable electrode fulfills the 10-20 system. During setup, the EEG headset 100 can regularly sample these potentiometers to track the position of each adjustable electrode and provide feedback to the EEG test administrator in (near) real-time directly through the EEG headset 100 or through an EEG portal at the connected computing device until the EEG headset 100 is properly configured according to the 10-20 system (or other electrode placement standard). Furthermore, the EEG headset 100 (and/or the native EEG test application) can reject a request to start an EEG test at the EEG headset 100 until all electrodes in the EEG headset 100 are confirmed in their proper positions according to the 10-20 system. (Similarly, the EEG headset 100 and/or the native EEG test application can reject a request to start an EEG test at the EEG headset 100 until all electrodes specified as active in the upcoming EEG test or at least a threshold number of electrodes specified in the upcoming EEG headset are confirmed in their proper positions according to the 10-20 system, such as within a tolerance of three millimeters or 5%. The EEG headset 100 (and/or the native EEG test application) can implement similar methods and techniques throughout the subsequent EEG test performed at the EEG headset 100 to confirm that adjustable electrodes within the band 121 remain in proper position on the user's head and to provide related notifications to the EEG test administrator in (near) real-time until the EEG test is complete.

However, each adjustable electrode and each band in the EEG headset 100 can include any other type of positional sensor arranged in any other way in the EEG headset 100 and configured to output a signal representative of the relative position of its corresponding electrode and the length of each band in the EEG headset 100. For example, rather than a linear potentiometer, each band can include a mechanical, optical, or magnetic optical encoder, such as in linear or rotational format.

4.7 Sense Electrode Contact Force

In this variation (and other variations described below), the EEG headset 100 can also include a pressure sensor interposed between each sense electrode and its corresponding band. For example, for each sense electrode, the EEG headset can include a conductive foam, diaphragm-type, or piezoelectric pressure sensor configured to output a signal representative of a force applied by the sense electrode to the user's skin. The EEG headset can thus sample each pressure sensor to confirm that each sense electrode is applying at least a minimum force (or pressure) to the user's skin, that each sense electrode is applying between a threshold minimum force and a threshold maximum force to the user's skin, and/or that all sense electrodes in the EEG headset are applying substantially similar forces (or pressures) to the user's skin. The EEG headset (or the native EEG test application executing on the connected computing device) can then serve prompts to the EEG test administrator to confirm that each sense electrode is properly depressed onto the user's skin and/or to prompt the EEG test administrator to tighten or loosen select electrodes in order to achieve these applied force targets before beginning the EEG test.

4.8 Contact Loss Feedback

The EEG headset 100 can additionally or alternatively include light elements 170 facing outwardly from the bands adjacent corresponding electrodes, and the controller 184 can selectively activate these light elements 170 during an EEG test in order to visually indicate to an EEG test administrator when an electrode has lost contact with the user's skin. For example, the EEG headset 100 can include a first light element 170 arranged on the first band 121 adjacent the first electrode 140 and facing outwardly from the first band 121; and the controller 184 can read a signal from the first electrode 140, characterize contact quality between the first electrode 140 and a scalp of a user (e.g., based on features in this signal or based on an output of a pressure sensor coupled to the first electrode 140), and selectively activate the first light element 170 in response to detecting improper contact between the first electrode 140 and the scalp of the user, as described in U.S. patent application Ser. No. 15/351,016.

5. Fixed Sense Electrodes

In one variation, rather than a single discrete electrode at each adjustable electrode position described below, the EEG headset includes a linear array of multiple discrete electrodes (hereinafter an "electrode array") fixedly coupled to a band 121, and the EEG headset 100 (e.g., the controller 184) or external computing device connected to the EEG headset 100 selectively activates one electrode in each electrode array that best realizes electrode placement rules of the 10-20 EEG electrode configuration (or other EEG electrode placement standard). For example, the EEG headset 100 includes one electrode array at each of the: F7 and F8 electrode positions along the first band 121; the F3 and F4 electrode positions along the second band 122; the C3 and C4 electrode positions along the third band 123; the P3 and P4 electrode positions along the fourth band 124; and the O1 and O2 electrode positions along the fifth band 125.

In this variation, each electrode array can include a set of discrete sense electrodes—as described above—packaged into a single block with the center-to-center distances between adjacent electrodes equal to or less than an electrode positional tolerance defined by the 10-20 system. For example, for an electrode positional tolerance of +/−five millimeters, the center-to-center distance between adjacent sense electrodes in one electrode array can be less than or equal to ten millimeters such that a particular electrode in an electrode array may fall within the positional tolerance of a target electrode positional—according to the 10-20 system—and can then be activated accordingly, as described below. Furthermore, each sense electrode in an electrode array can include: a discrete substrate; a discrete set of electrically-conductive prongs extending from a first side of the substrate; and a discrete amplifier coupled to the substrate opposite the set of prongs and configured to amplify an electrical signal passing through the set of prongs. In particular, each electrode in an electrode array can be electrically isolated from other electrodes in the electrode array and can be selectively activated and deactivated independently of other electrodes in the same electrode array, such as by connecting and disconnecting the electrode from both power and ground terminals in the EEG headset 100.

5.1 Manual Activation

In one implementation, an EEG test administrator (or the user, etc.) enters a final adjustment position for each band—such as read from a scale arranged between the left and right junctions 110, 112 and each band—into the native EEG test application executing on the connected computing device; and the native EEG test application maps a final adjustment position for each band to known positions of electrode arrays along each band to select a particular electrode in each electrode array that best fulfills electrode position rules specified by the 10-20 system.

In one example, for the second band 122 that supports an F3 electrode array at the F3 position, an F4 electrode array at the F4 position, and a fixed Fz electrode at the Fz position, the native EEG test application accesses a lookup table or electrode map defining a position of each electrode in each of the F3 and F4 electrode arrays relative to the fixed Fz electrode. The native EEG test application can also retrieve a lookup table or parametric model (e.g., a mathematical equation) linking adjustment positions of the second band 122 to an effective distance between the fixed Fz electrode and the fixed T3 (or T4) electrode. The native EEG test application then divides this effective distance by two, selects a particular electrode from the electrode array at the F4 position that falls nearest this halved effective distance, activates this particular electrode in the F4 electrode array, and deactivates all other electrodes in the F4 electrode array. The native EEG test application can implement similar methods and techniques to activate a particular electrode in the F3 electrode array.

Alternatively, the native EEG test application can access a lookup table or other model that directly specifies electrodes in electrode arrays throughout the EEG headset 100 that meet electrode position rules of the 10-20 system for specific adjustment positions of each band. The native EEG test application can then implement similar methods and techniques described above to select specific electrodes in electrode arrays at the F7, F8, C3, C4, P3, P4, O1, and O2 positions along the first, third, fourth, and fifth bands. The native EEG test application can then push a command to activate these select electrodes back to the EEG headset 100, which can implement these electrode specifications during the subsequent EEG test.

Yet alternately, in this implementation, the native EEG test application can transmit final band adjustments—entered by the EEG test administrator into the native EEG test application—to the EEG headset 100, and a controller 184 within the EEG headset 100 can implement the foregoing methods and techniques locally to selectively activate and deactivate electrodes within electrode arrays throughout the EEG headset 100 based on these final band adjustments in order to achieve a best approximation of the 10-20 system (or other biosignal acquisition system) during the current EEG test.

5.2 Automatic Activation

Alternatively, each band in the EEG headset 100 can include a linear potentiometer interposed between the band 121 and the left (or right) junction, wherein the internal electrical resistance of each linear potentiometer changes as a function of the position of the band 121, such as a function of a distance from a first end of the band 121 to the left junction 110. The EEG headset 100 (e.g., a controller 184) can: sample linear potentiometers coupled to each band and transform voltages read from these linear potentiometers into adjustment positions of each band; and then transform a voltage read across each linear potentiometer (or a resistance of each potentiometer) into an adjustment position of the corresponding band, such as by passing the voltage read from the potentiometer into a lookup table or mathematical model. The controller 184 can then implement methods and techniques described above to select particular electrodes in each electrode array that best fit the 10-20 system. Alternatively, the EEG headset 100 can access a lookup table that directly maps a voltage read across each potentiometer (or a resistance of each potentiometer) to a particular electrode in each electrode array on the corresponding band, as described above. The EEG headset 100 can then activate these select electrodes and deactivate all other electrodes in the electrode arrays in the EEG headset 100 during the subsequent EEG test.

However, in this variation each band can include a positional sensor of any other type, such as a mechanical, optical, or magnetic optical encoder, as described above.

6. Replacement Electrodes Tips

In one implementation, the sense electrodes include replaceable tips. For example, each sense electrode can include a magnetic element 143 adjacent or behind a terminal electrically coupled to an input of an amplifier within the sense electrode and configured to retain a removable electrode tip containing a ferrous element 148. In this example, the magnetic element 143 in each sense electrode can be configured to retain any of: an elastic bristle electrode tip; a rigid prong electrode tip; a flat contact disk electrode tip; a domed contact disk electrode tip; and/or any other type or geometry of electrode tip. Alternatively, each electrode can include a mechanical electrode tip retainer (e.g., a latch) configured to accept, retain, and then release an electrode tip.

In the variation described above in which the EEG headset 10 includes electrode arrays, each electrode array can similarly include a magnetic element 143 or other mechanical feature configured to retain a removable array of like electrode tips 144 containing a ferrous element 148 or other mating feature. In this example, each array of electrode tips 144 can include multiple discrete and electrically isolated electrode tips 144 arranged in a single assembly that can be installed and then removed from an electrode array.

However, each electrode or electrode array in the EEG headset 100 can be configured to transiently receive electrode tips 144 (e.g., replacement electrode tips) of any other type or geometry.

7. Control Module

In one variation shown in FIGS. 1 and 3, the EEG headset 100 further includes a controller 184, a signal processor, a battery, and/or a wireless communication module 183 arranged within a control module 180 coupled to or physically coextensive with the fifth band 125 (or with the central body described above). Generally, the control module 180 can contain various controls, communication, and power components of the EEG headset 100 and can be mounted to or integrated into the rearmost (e.g., the fifth) band in order to: maintain access to various related controls and ports;

limiting obstruction to the user's vision and movements; and/or to counterbalance the EEG headset 100, thereby improving stability of the EEG headset 100 during an EEG test.

For example, the EEG headset 100 can include: a fifth band 125 spanning the left junction 110 and the right junction 112 and configured to extend proximal a base of a skull of a user when the EEG headset 100 is worn on the head of the user; a housing 181 arranged on the fifth band 125; and a battery 182, a controller 184, and a wireless transmitter 183 arranged in the housing 181, as shown in FIGS. 1 and 3. In this example, the controller 184 can be configured to read a set of analog sense signals from active electrodes within the EEG headset 100 (e.g., the first electrode 140, the second electrode 152, the third electrode 153, etc.) during an EEG test performed at the EEG headset 100, such as described in U.S. patent application Ser. No. 15/351,016. In this example, the wireless transmitter 183 can wirelessly transmit digital representations of the set of analog sense signals recorded by the controller 184, such as to a remote database via a local hub or wireless router in real-time during the EEG test.

The EEG headset 100 can also include a set of wires passing from the control module 180 (or the fifth band 125) to sense electrodes in other bands throughout the EEG headset 100 and configured to communicate sense signals from the sense electrodes back to the controller 184 and/or signal processor.

However, the control module 180 can be arranged within or distributed across the EEG headset 100 in any other form or format. Elements of the control module 180 can also be integrated into the connected computing device (e.g., the controller 184 or processor), and sensor signals and control commands can be communicated between the connected computing device and the EEG headset 100 via a wired or wireless connection.

8. Drive and Reference Electrodes

The EEG headset 100 can also include a reference electrode and a drive electrode (or a "driven right leg" electrode), as described in U.S. patent application Ser. No. 15/351,016. Like each sense electrode, the drive electrode can define a dry EEG sensor, and including: a substrate; an electrode tip extending from or (transiently) electrically coupled to a first side of the substrate; and an amplifier coupled to the substrate opposite the electrode tip and configured to amplify an electrical signal detected by the electrode tip. In this implementation, the amplifier can output a low-impedance reference signal that follows a high-impedance reference signal read at the electrode tip to the signal processor or controller 184 described above. However, the drive electrode can include any other type of dry- or wet-type EEG electrode and can output any other signal to the signal processor or controller 184. The drive electrode can include a fixed or interchangeable electrode tip of a similar geometry.

In one implementation, the drive electrode is fixedly mounted to the first band 121 between sense electrodes in the FP1 and FP2 positions. Alternatively, the drive electrode can be mounted to a beam that pivots or extends downwardly from the right junction 112 or from the right side of the control module 180; the beam can be configured to locate and depress the drive electrode onto the user's skin, such as below the user's right ear. The reference electrode can be similarly mounted to a beam that pivots or extends downwardly from the left junction 110 or from the left side of the control module 180 to locate and depress the reference electrode onto the user's skin, such as below the user's left ear.

Alternatively, the EEG headset 100 can include a sixth band configured to drop (e.g., pivot downwardly) from the fifth band 125, and the drive and reference electrodes can be mounted to the sixth band. In yet another implementation, the drive and reference electrodes can be coupled to loose, elastic wires configured to (transiently) plug into the control module 180 and can be configured to stick onto or to be taped onto the user's skin substantially remotely from the user's scalp. However, the drive and reference electrodes can be arranged within the EEG headset 100 in any other way.

9. Optical Detector

In one variation, the EEG headset 100 further includes an optical detector 190 facing outwardly from the front band (e.g., configured to lie across a user's forehead) and configured to output a signal that follows variations in local light intensity. In this variation, the controller 184 can record a first EEG signal output by a first electrode 140 in the EEG headset 100 to a first sense channel and record a second EEG signal output by a second electrode 152 in the EEG headset 100 to a second sense channel; record a third EEG signal output by the third electrode 153 in the EEG headset 100 to a third sense channel; etc., as described above. The controller 184 can also record a signal output by the optical detector 190 to a strobe channel synchronized to the first sense channel, the second sense channel, and the third sense channel.

Therefore, in this variation, the optical detector 190 can output a signal that follows the intensity of light output by an active strobe light (or "photic stimulator") facing a user during an EEG test; and the controller 184 can record the output of the optical detector 190 to a strobe channel temporally synchronized to sense channels for each sense electrodes in the EEG headset 100. For example, during each sampling period (e.g., at a rate of 500 Hz) during an EEG test, the controller 184 can: write digital representations of the voltage at each sense electrode during the current sampling period to its corresponding sense channel; read the analog output of the optical detector 190 during the current sampling period; write a HI (or "1") value to the strobe channel if the value of the analog output signal of the optical detector 190 exceeds a threshold value; and write a LO (or "0") value to the strobe channel if the value of the analog output signal of the optical detector 190 is less than a threshold value. In this example, the controller 184 can repeat this process for each sampling period to record synchronized, temporal representations of electrical activity at various regions of the user's brain and strobe light activity near the user over the duration of an EEG test.

10. Tape

In one variation, the EEG headset 100 accompanies a measurement tape. In this variation, the measurement tape can include: a first side containing a centerline measurement scale; and a second side containing a circumferential measurement scale. During setup, an EEG test administrator can run the measurement tape—first side facing up—from the base of a user's skull to the user's forehead, read a value from the measurement tape representing this centerline distance, and then set band adjusters in the second, third, and fourth bands in the EEG headset 100 such that their corresponding scales read this value. The EEG test administrator can thus adjust the second, third, and fourth bands—that extend over the top of the user's skull—to initial positions that may accept the user's upper skull shape and size and that may approximate final adjustment settings of the EEG headset 100 for the user, as shown in FIG. 7.

The EEG test administrator can then run the measurement tape—second side facing out—from around the circumference of the user's skull just above the user's ears, read a value from the measurement tape representing this circumferential distance, and then set band adjusters in the first and fifth bands in the EEG headset 100 such that their corresponding scales read this value. The EEG test administrator can thus adjust the first and fifth bands—that wrap around the circumference of the user's skull—to initial positions that may accept the full breadth and length of the user head and that may approximate final adjustment settings of the EEG headset 100 for the user.

Once initial adjustment positions of the first, second, third, fourth, and fifth bands of the EEG headset 100 are thus set based on values read from the measurement tape, the EEG test administrator can place the EEG headset 100 onto the user's head and make final adjustments to the bands via the band adjusters to achieve proper contact between the sense electrodes and the user's skin.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system for collecting biosignal data comprising:
a controller;
an electrode body comprising:
  a proximal end coupled to a first node of a headset;
  a first magnetic element arranged on a distal end of the electrode body, comprising a conductive surface, and electrically coupled to the controller; and
a kit of electrode tips, each electrode tip in the kit of electrode tips comprising a secondary magnetic element configured to transiently couple the electrode tip to the first magnetic element at the distal end of the electrode body and to communicate a sense signal from the electrode tip into the electrode body via the first magnetic element, the kit of electrode tips comprising:
  a first electrode tip comprising a first set of contact surfaces in a first configuration; and
  a second electrode tip comprising a second set of contact surfaces in a second configuration;
a set of support blocks:
  rigidly mounted to the headset;
  extending inwardly from the headset; and
  configured to support a weight of the headset on a scalp of a user; and
a spring element coupled to the electrode body such that:
  in a resting position, the spring element drives the distal end of the electrode body away from the headset and past a distal surface of a support block within the set of support blocks with a force, within a range of target electrode tip forces, decoupled from the weight of the headset; and
  in a compressed position, the spring element enables displacement of the electrode body toward the headset.

2. The system of claim 1:
wherein the first set of contact surfaces of the first electrode tip defines a first set of pronged contact elements of a first length;
wherein the second set of contact surfaces of the second electrode tip defines a second set of pronged elements of a second length greater than the first length; and
wherein the spring element is configured to:
  drive the first set of contact surfaces of the first electrode tip into the scalp of the user with a first force within the range of target electrode tip forces when the first electrode tip is transiently installed on the first magnetic element; and
  drive the second set of contact surfaces of the second electrode tip into the scalp of the user with a second force approximating the first force when the second electrode tip is transiently installed on the first magnetic element.

3. The system of claim 1:
wherein the first set of a contact surfaces of the first electrode tip defines a first contact area configured to contact the scalp of the user;
wherein the second set of a contact surfaces of the second electrode tip defines a second contact area configured to contact the scalp of the user; and
wherein each support block in the set of support blocks defines a contact area, greater than the first contact area and the second contact area, configured to contact the scalp of the user and to support a portion of the weight of the headset on the scalp of the user.

4. A system for collecting biosignal data, comprising:
a controller;
a headset comprising a band extending between a first junction and a second junction on the headset;
a support block:
  rigidly mounted to the band; and
  comprising a distal surface:
    inwardly offset from the band by a fixed distance;
    configured to rest against a head of a user; and
    configured to support a portion of a weight of the headset on the head of the user; and
an electrode:
  arranged on the band adjacent the support block;
  extending inwardly from the band; electrically coupled to controller; and
  comprising:
    an electrode tip comprising a set of contact surfaces configured to contact a scalp of the user;

an electrode body configured to transiently couple to the electrode tip and to communicate a sense signal from the electrode tip to the controller; and a spring element coupled to the electrode body such that:

in a resting position, the spring element locates the set of contact surfaces of the electrode tip inwardly past the distal surface of the support block; and in a compressed position, the spring element enables displacement of the electrode toward the band responsive to contact between the electrode tip and the scalp of the user.

5. The system of claim 4:

further comprising a retraction shoulder extending laterally from the electrode body between the band and the electrode tip; and wherein the spring element is:

interposed between the band and the electrode body; and configured to support manual retraction of the electrode tip past the distal surface of the support block toward the band in order to separate the electrode tip from the scalp of the user.

6. The system of claim 4, wherein the support block is configured to support the portion of the weight of the headset on the head of the user to decouple a force, applied by the spring element to the electrode tip, from the weight of the system and from a proportion of electrodes, arranged on the headset, in contact with the scalp of the user.

* * * * *